US011927547B2

United States Patent
Meng et al.

(10) Patent No.: US 11,927,547 B2
(45) Date of Patent: Mar. 12, 2024

(54) DETECTION SYSTEM AND DETECTION METHOD FOR WATER CONTENT AND CONDUCTIVITY

(71) Applicant: JIANGSU MAIHE INTERNET OF THINGS TECHNOLOGY CO., LTD, Jiangsu (CN)

(72) Inventors: Min Meng, Jiangsu (CN); Yuxiao Meng, Jiangsu (CN)

(73) Assignee: JIANGSU MATHE INTERNET OF THINGS TECHNOLOGY CO., LTD., Jiangsu (CN)

( * ) Notice: Subject to any disclaimer, the term of this patent is extended or adjusted under 35 U.S.C. 154(b) by 875 days.

(21) Appl. No.: 16/997,962

(22) Filed: Aug. 20, 2020

(65) Prior Publication Data
US 2020/0378903 A1  Dec. 3, 2020

Related U.S. Application Data

(63) Continuation of application No. PCT/CN2018/125426, filed on Dec. 29, 2018.

(51) Int. Cl.
*G01N 22/04* (2006.01)
*G01N 33/28* (2006.01)
*G01R 27/02* (2006.01)
*G01N 27/22* (2006.01)

(52) U.S. Cl.
CPC ......... *G01N 22/04* (2013.01); *G01N 33/2847* (2013.01); *G01R 27/02* (2013.01); *G01N 27/221* (2013.01)

(58) Field of Classification Search
CPC .. G01N 22/04; G01N 33/2847; G01N 27/221; G01R 27/02
See application file for complete search history.

(56) References Cited

U.S. PATENT DOCUMENTS

| 10,067,091 | B2* | 9/2018 | Hassell, Jr. | ........ G01N 33/2847 |
| 2020/0003730 | A1* | 1/2020 | Winecki | ............... G01N 33/241 |

FOREIGN PATENT DOCUMENTS

| CN | 104141491 A | 11/2014 |
| CN | 106706670 A | 5/2017 |

* cited by examiner

*Primary Examiner* — Reena Aurora

(57) ABSTRACT

A detection system and a detection method for water content and conductivity are provided. The detection system includes a double-sided microstrip circuit and a detection circuit; the double-sided microstrip circuit includes a shielding ground layer; a measurement side circuit and a reference side circuit are respectively arranged at two sides of the shielding ground layer and both include an insulating layer and a wire; the detection circuit includes a signal generator connected to a microprocessor and a power divider; two output ends and a ground end of the power divider are respectively electrically connected to first ends of a reference wire, a measurement wire, and the shielding ground layer; a second end of the reference wire is connected to an amplitude and phase discriminator through a phase shifter; second ends of the measurement wire and the shielding ground layer are directly connected to the amplitude and phase discriminator.

6 Claims, 1 Drawing Sheet

DETECTION SYSTEM AND DETECTION METHOD FOR WATER CONTENT AND CONDUCTIVITY

CROSS REFERENCE OF RELATED APPLICATION

The application is a continuation application of a PCT application No. PCT/CN2018/125426, filed on Dec. 29, 2018; and claims the priority of Chinese Patent Application CN 201811600592.5, filed to the State Intellectual Property Office of China (SIPO) on Dec. 26, 2018, the entire content of which are incorporated hereby by reference.

BACKGROUND OF THE PRESENT INVENTION

Field of Invention

The present invention relates to a technical field of material parameter detection, and more particularly to a detection system and a detection method for water content and conductivity.

Description of Related Arts

In various industries such as the petroleum industry and chemical industry, it is necessary to detect the water content and the conductivity of the materials during the production process; in particular, for the petroleum industry, the water content and the mineralization degree of the crude oil are very important indexes, which are not only directly related to the production benefits, but also are the important data for the formation data analysis. The conventional detection methods comprise the impedance method, the capacitance method, the radio frequency attenuation method, etc. However, the above methods have following major problems. The above methods are unable to realize a full-range detection of 0-100%, especially the detection under the condition of high water content. Moreover, the above methods are greatly influenced by the mineralization degree and cannot conduct detection under the high mineralization degree condition. Furthermore, the overall detection precision of the above methods is relatively low.

SUMMARY OF THE PRESENT INVENTION

In order to solve problems that conventional methods cannot realize a full-range accurate detection for water content and mineralization degree, an object of the present invention is to provide a detection system for water content and conductivity, which is able to realize the full-range detection for the water content and the mineralization degree with guaranteeing a detection precision. Meanwhile, the present invention further provides a corresponding detection method.

Technical solutions of the present invention are described as follows.

A detection system for water content and conductivity comprises a double-sided microstrip circuit and a detection circuit, wherein: the double-sided microstrip circuit comprises a shielding ground layer; a measurement side circuit is arranged at one side of the shielding ground layer, and a reference side circuit is arranged at the other side of the shielding ground layer; both of the measurement side circuit and the reference side circuit comprise an insulating layer and a wire; lengths and materials of a measurement wire of the measurement side circuit and a reference wire of the reference side circuit are uniform; the detection circuit comprises a signal generator connected to a microprocessor; the signal generator is connected to an input end of a power divider; two output ends and a ground end of the power divider are respectively electrically connected to a first end of the reference wire, a first end of the measurement wire, and a first end of the shielding ground layer; a second end of the reference wire is connected to a first input end of an amplitude and phase discriminator through a phase shifter; a second end of the measurement wire and a second end of the shielding ground layer are respectively connected to a second input end and a ground end of the amplitude and phase discriminator; an output end of the amplitude and phase discriminator is connected to the microprocessor; the measurement side circuit contacts a measured medium, and the reference side circuit contacts air or a low-dielectric constant material.

Preferably, materials and thicknesses of a measurement side insulating layer of the measurement side circuit and a reference side insulating layer of the reference side circuit are uniform;

the signal generator outputs a variable-frequency signal of 200-960 MHz; the power divider divides the signal into two signals with a proportion of 1:1, and respectively output to the measurement side circuit and the reference side circuit;

the first end of the measurement wire is connected to the power divider through a first high-frequency shielding wire which penetrates through the measurement side insulating layer, the shielding ground layer and the reference side insulating layer; the second end of the measurement wire is connected to the amplitude and phase discriminator through a second high-frequency shielding wire which penetrates through the measurement side insulating layer, the shielding ground layer and the reference side insulating layer;

sealing insulation through holes, which match with the high-frequency shielding wires, are provided on the shielding ground layer;

a sealing cover is arranged at the reference side circuit; and the low-dielectric constant material is filled inside the sealing cover; and the microprocessor is connected to a communication circuit.

A detection method for water content and conductivity comprises steps of:

(1) by the microprocessor, controlling the signal generator to output a microwave signal; by the power divider, dividing the microwave signal into two signals and respectively outputting to the measurement side circuit and the reference side circuit;

(2) firstly calibrating a phase difference signal respectively under a water-free condition and a pure water condition, obtaining values of the phase difference signal respectively under water contents of 0% and 100%, and storing into the microprocessor; wherein if the measured medium, which the measurement side circuit contacts, contains water, a transmission speed of a microwave signal on the measurement wire is reduced, and the microwave signal on the measurement wire produces a phase shift with a microwave signal on the reference wire; through comparing phases of the microwave signals outputted by the measurement wire and the reference wire, outputting a phase difference signal by the amplitude and phase discriminator and then transmitting to the microprocessor, wherein the phase difference signal corresponds to a phase difference between the microwave signals of the measurement wire and the reference wire; through calculating by the microprocessor, obtaining a water content of the measured medium; and (3) firstly calibrating an amplitude difference signal respectively under a water-free condition and a condition with a full measuring range of conductivity, obtaining minimum and maximum calibration values of the amplitude difference signal, and storing into the microprocessor; wherein if the measured medium, which the measurement side circuit contacts, contains water or minerals, a conductivity of the measured medium is increased, and an amplitude of the microwave signal of the measurement wire is attenuated relative to an amplitude of the microwave signal of the reference wire; through comparing the amplitudes of the microwave signals outputted by the measurement wire and the reference wire, outputting an amplitude difference signal by the amplitude and phase discriminator and then transmitting to the microprocessor, through calculating by the microprocessor, obtaining the conductivity of the measured medium; and obtaining a corresponding mineralization rate according to the conductivity.

According to the system and the method provided by the present invention, the measurement side circuit contacts the measured medium, and the reference side circuit contacts air or the low-dielectric constant material; the microwave signals distributed by the power divider pass through the measurement wire and the reference wire whose lengths and materials are both uniform; depending on whether the measured medium contains water or minerals, the changes of the microwave signals on the measurement wire and the reference wire are obtained; through comparing by the amplitude and phase discriminator, the accurate detection results are obtained; the phase shifter can adjust the phase of the microwave signal on the reference wire, playing the calibration and zeroing functions, so as to realize the full-range detection of the water content and the mineralization degree. Furthermore, the materials and the thicknesses of the measurement side insulating layer and the reference side insulating layer are uniform; the power divider divides the signal from the signal generator into two signals with a proportion of 1:1, so that the detection becomes more accurate and reliable; under different temperatures, although the dielectric constants of the materials of the insulating layers will change, the phase changes brought by the measurement side circuit and the reference side circuit are equivalent, which can automatically compensate the system measurement error brought by the temperature and guarantee the detection precision.

DETAILED DESCRIPTION OF THE PREFERRED EMBODIMENT

Figure 1:
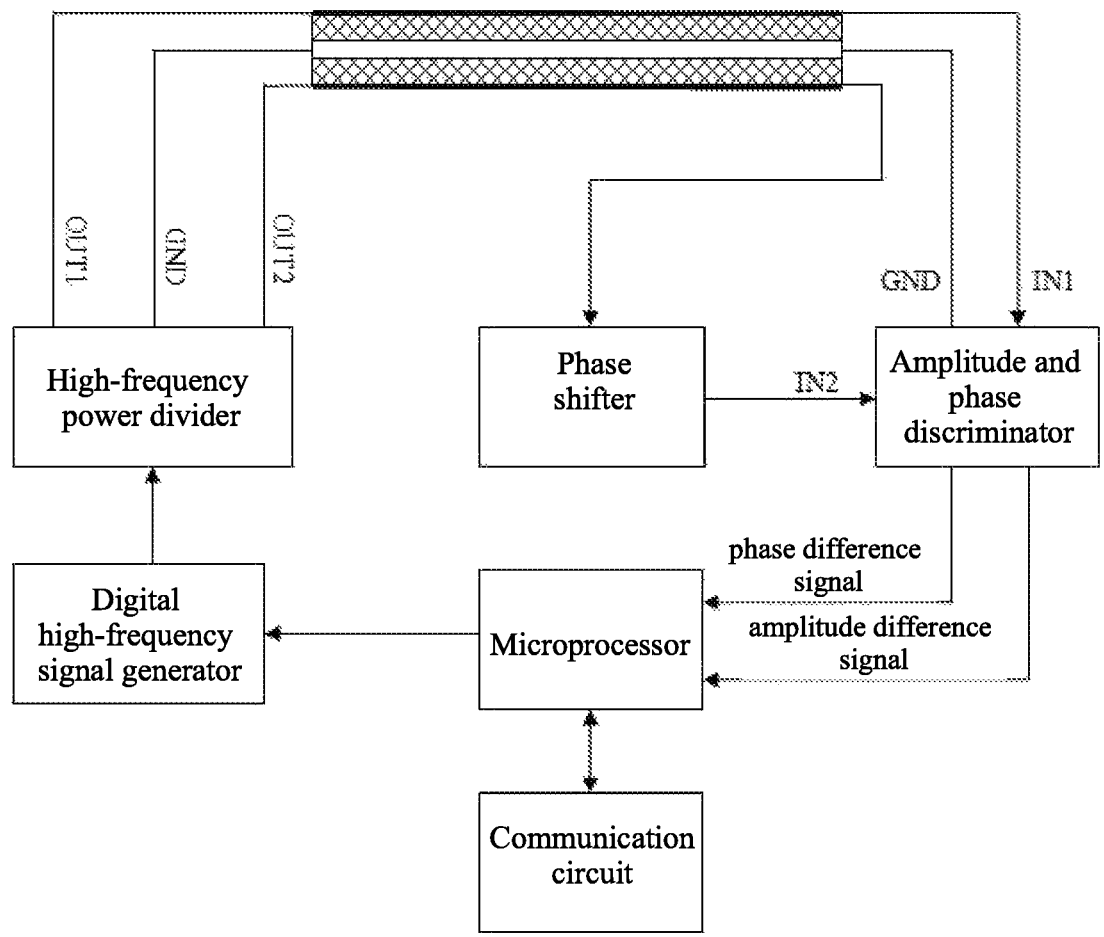
FIG. 1 is a principle diagram of the present invention.
Figure 2:
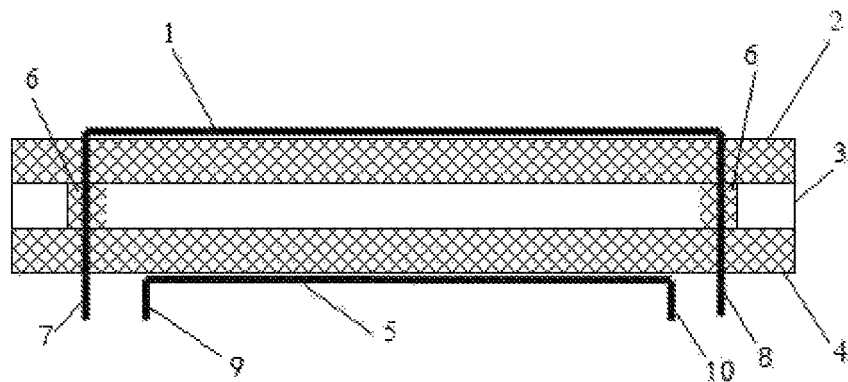
FIG. 2 is a structural sketch view of a double-sided microstrip circuit according to the present invention.

Referring to FIG. 1 and FIG. 2, according to the preferred embodiment of the present invention, a detection system for water content and conductivity is provided, comprising a double-sided microstrip circuit and a detection circuit, wherein: the double-sided microstrip circuit comprises a shielding ground layer 3; a measurement side circuit is arranged at one side of the shielding ground layer 3, and a reference side circuit is arranged at the other side of the shielding ground layer 3; the measurement side circuit comprises a measurement side insulating layer 2 and a measurement wire 1; the reference side circuit comprises a reference side insulating layer 4 and a reference wire 5; lengths and materials of the measurement wire 1 of the measurement side circuit and the reference wire 5 of the reference side circuit are uniform; materials and thicknesses of the measurement side insulating layer 2 and the reference side insulating layer 4 are uniform; the detection circuit comprises a digital high-frequency signal generator connected to a microprocessor; the digital high-frequency signal generator is connected to an input end of a high-frequency power divider; two output ends OUT1 and OUT2 and a ground end GND of the high-frequency power divider are respectively electrically connected to a first end of the measurement wire 1, a first end of the reference wire 5, and a first end of the shielding ground layer 3; a second end of the reference wire 5 is connected to a second input end IN2 of an amplitude and phase discriminator through a phase shifter; a second end of the measurement wire 1 and a second end of the shielding ground layer 3 are respectively connected to a first input end IN1 and a ground end GND of the amplitude and phase discriminator; an output end of the amplitude and phase discriminator outputs a phase difference signal and an amplitude difference signal, and transmits to the microprocessor; the measurement side circuit contacts a measured medium, and the reference side circuit contacts air or a low-dielectric constant material; the low-dielectric constant material is a dielectric medium having a relatively low dielectric constant k (lower than silicon dioxide, k=3.9), which is mainly applied in the microelectronic field; when contacting the low-dielectric constant material, a sealing cover is required to be arranged outside, and the low-dielectric constant material is filled inside the sealing cover.

Because the measurement side circuit needs to contact the measured medium and the measured medium is liquid such as crude oil, in order to guarantee reliable detection, after being led to the reference side circuit, the two ends of the measurement wire 1 are required to be electrically connected to the high-frequency power divider and the amplitude and phase discriminator. Therefore, a following structure is adopted. The first end of the measurement wire 1 is connected to the high-frequency power divider through a first measurement side high-frequency shielding wire 7 which penetrates through the measurement side insulating layer 2, the shielding ground layer 3 and the reference side insulating layer 4; the second end of the measurement wire 1 is connected to the amplitude and phase discriminator through a second measurement side high-frequency shielding wire 8 which penetrates through the measurement side insulating layer 2, the shielding ground layer 3 and the reference side insulating layer 4; sealing insulation through holes 6, which match with the measurement side high-frequency shielding wires 7 and 8, are provided on the shielding ground layer 3; because the two measurement side high-frequency shielding wires 7 and 8 penetrate to the reference side circuit, the length of the reference wire 5 is required to be consistent with that of the measurement wire 1. Therefore, as shown in FIG. 1 and FIG. 2, reference side high-frequency shielding wires 9 and 10 are arranged at two sides of the reference wire 5.

The signal generator outputs a variable-frequency signal of 200-960 MHz; the power divider divides the signal into two signals with a proportion of 1:1, and respectively output to the measurement side circuit and the reference side circuit.

A detection method for water content and conductivity comprises steps of:

(1) by the microprocessor, controlling the signal generator to output a microwave signal of 200-960 MHz; by the power divider, dividing the microwave signal into two signals with a proportion of 1:1 and respectively outputting to the measurement side circuit and the reference side circuit; wherein: according to a microwave transmission theory, a formula of a microwave transmission speed is:

$$V = \frac{c}{\sqrt{\varepsilon\mu}}$$

wherein: c is a velocity of light; ε is a mixed dielectric constant; μ is a magnetic conductivity; the magnetic conductivity is 1 and can be ignored, so that the microwave transmission speed depends on the mixed dielectric constant; a mixed dielectric constant of the reference side circuit consists of a dielectric constant of the reference side insulating layer and a dielectric constant of air or a low-dielectric constant material filler, which is a fixed value under a constant temperature; a mixed dielectric constant of the measurement side circuit consists of a dielectric constant of the measurement side insulating layer and a dielectric constant of the measured medium;

(2) wherein if media, which the measurement side circuit and the reference side circuit contact, are same and water-free, the microwave signals on the measurement wire and the reference wire have the same transmission speed and same phase;

if the measured medium, which the measurement side circuit contacts, contains water, the transmission speed of the microwave signal on the measurement wire is reduced, and the microwave signal on the measurement wire produces a phase shift with the microwave signal on the reference wire; through comparing by the amplitude and phase discriminator, obtaining a water content of the measured medium, specifically comprising steps of: before detecting the water content of the measured medium, calibrating a phase difference signal respectively with a water-free medium and pure water, for example pure oil and pure water, wherein a phase direct-current voltage signal Vp outputted by the amplitude and phase discriminator corresponds to a phase difference between the microwave signals of the measurement wire and the reference wire; through calibrating, obtaining a phase difference signal Vpo with pure oil and a phase difference signal Vpw with pure water, namely calibrating the phase difference signal under the water content of 0-100%, wherein: Vpo<Vpw and the two parameters are stored in the microprocessor; during real-time detection, a phase difference signal is Vpx; and the water content α of the measured medium is obtained through a formula of:

$$\alpha=(Vpx-Vpo)/(Vpw-Vpo);$$

(3) wherein if the media, which the measurement side circuit and the reference side circuit contact, are same and water-free, conductivity of the media is same, and an amplitude and an attenuation degree of the microwave signals on the measurement wire and the reference wire are same, wherein: because the medium of the reference side circuit is constant and has the low conductivity, close to zero, the amplitude and the attenuation degree of the microwave signal on the reference wire are constant; if the measured medium, which the measurement side circuit contacts, contains water or minerals, the conductivity of the measured medium is increased, and the amplitude of the microwave signal of the measurement wire is attenuated relative to the amplitude of the microwave signal of the reference wire; through comparing by the amplitude and phase discriminator, obtaining an amplitude direct-current voltage signal corresponding to a logarithm of an amplitude ratio; collecting the amplitude direct-current voltage signal by the microprocessor, then calculating the conductivity of the measured medium, and obtaining a corresponding mineralization rate according to the conductivity, wherein: because a corresponding relationship exists between the conductivity and the mineralization rate, the corresponding mineralization rate can be obtained through calculating the conductivity, specifically comprising steps of: before detecting the conductivity of the measured medium, calibrating an amplitude difference signal with standard conductivity solutions, for example pure water having a conductivity of 0 and a solution having a high conductivity, wherein the detailed conductivity is determined by a measuring range, and the amplitude direct-current voltage signal Va outputted by the amplitude and phase discriminator corresponds to an amplitude difference between the microwave signals of the measurement wire and the reference wire; through calibrating, obtaining an amplitude difference signal Va0 with the conductivity being 0, and an amplitude difference signal Va1 with the full measuring range of conductivity, wherein: Va0>Va1 and the two parameters are stored in the microprocessor; during real-time detection, an amplitude difference signal is Vax; and the conductivity σ of the measured medium is obtained through a formula of:

$$\sigma=(Va0-Vax)*\text{range}/(Va0-Va1),\text{ wherein: range represents a full measuring range of conductivity of a device.}$$

Because the microprocessor is connected to a communication circuit, detection results can be transmitted through the communication circuit.

What is claimed is:

1. A detection system for water content and conductivity of a measured medium, comprising a double-sided microstrip circuit and a detection circuit, wherein: the double-sided microstrip circuit comprises a shielding ground layer; a measurement side circuit is arranged at one side of the shielding ground layer, and a reference side circuit is arranged at the other side of the shielding ground layer; both of the measurement side circuit and the reference side circuit comprise an insulating layer and a wire; lengths and materials of a measurement wire of the measurement side circuit and a reference wire of the reference side circuit are uniform; the detection circuit comprises a signal generator connected to a microprocessor; the signal generator is connected to an input end of a power divider; two output ends and a ground end of the power divider are respectively electrically connected to a first end of the reference wire, a first end of the measurement wire, and a first end of the shielding ground layer; a second end of the reference wire is connected to a first input end of an amplitude and phase discriminator through a phase shifter; a second end of the measurement wire and a second end of the shielding ground layer are respectively connected to a second input end and a ground end of the amplitude and phase discriminator; an output end of the amplitude and phase discriminator is connected to the microprocessor; the measurement side circuit contacts the measured medium, and the reference side circuit contacts air or a low-dielectric constant material; a measurement side insulating layer of the measurement side circuit is identical to a reference side insulating layer of the reference side circuit in materials and thicknesses; the signal generator outputs a variable-frequency signal of 200-960 MHz; the power divider divides the signal into two signals with a proportion of 1:1, and respectively output to the measurement side circuit and the reference side circuit.

2. The detection system, as recited in claim 1, wherein: the first end of the measurement wire is connected to the power divider through a first high-frequency shielding wire which penetrates through the measurement side insulating layer, the shielding ground layer and the reference side insulating layer; the second end of the measurement wire is connected to the amplitude and phase discriminator through a second high-frequency shielding wire which penetrates through the measurement side insulating layer, the shielding ground layer and the reference side insulating layer.

3. The detection system, as recited in claim 2, wherein: sealing insulation through holes, which match with the high-frequency shielding wires, are provided on the shielding ground layer.

4. The detection system, as recited in claim 1, wherein: a sealing cover is arranged at the reference side circuit; and the low-dielectric constant material is filled inside the sealing cover.

5. The detection system, as recited in claim 1, wherein the microprocessor is connected to a communication circuit.

6. A detection method for water content and conductivity with the detection system as recited in claim 1, comprising steps of:
  (1) by the microprocessor, controlling the signal generator to output a microwave signal; by the power divider, dividing the microwave signal into two signals and respectively outputting to the measurement side circuit and the reference side circuit;
  (2) firstly calibrating a phase difference signal respectively under a water-free condition and a pure water condition, obtaining values of the phase difference signal respectively under water contents of 0% and 100%, and storing into the microprocessor; wherein if the measured medium, which the measurement side circuit contacts, contains water, a transmission speed of a microwave signal on the measurement wire is reduced, and the microwave signal on the measurement wire produces a phase shift with a microwave signal on the reference wire; through comparing phases of the microwave signals outputted by the measurement wire and the reference wire, outputting a phase difference signal by the amplitude and phase discriminator and then transmitting to the microprocessor, wherein the phase difference signal corresponds to a phase difference between the microwave signals of the measurement wire and the reference wire; through calculating by the microprocessor, obtaining a water content of the measured medium; and
  (3) firstly calibrating an amplitude difference signal respectively under a water-free condition and a condition with a full measuring range of conductivity, obtaining minimum and maximum calibration values of the amplitude difference signal, and storing into the microprocessor; wherein if the measured medium, which the measurement side circuit contacts, contains water or minerals, a conductivity of the measured medium is increased, and an amplitude of the microwave signal of the measurement wire is attenuated relative to an amplitude of the microwave signal of the reference wire; through comparing the amplitudes of the microwave signals outputted by the measurement wire and the reference wire, outputting an amplitude difference signal by the amplitude and phase discriminator and then transmitting to the microprocessor, through calculating by the microprocessor, obtaining the conductivity of the measured medium; and obtaining a corresponding mineralization rate according to the conductivity.

* * * * *